(12) United States Patent
Cheng et al.

(10) Patent No.: US 8,753,756 B2
(45) Date of Patent: Jun. 17, 2014

(54) GREEN PHOSPHORESCENT IRIDIUM COMPLEXES, FABRICATION METHOD THEREOF AND ORGANIC LIGHT-EMITTING DIODES COMPRISING THE SAME

(75) Inventors: Chien-Hong Cheng, Hsinchu (TW); Jian-Lin Wu, Hsinchu (TW); Chuang-Yi Liao, Hsinchu (TW)

(73) Assignee: Chien-Hong Cheng, Hsinchu (TW)

( * ) Notice: Subject to any disclaimer, the term of this patent is extended or adjusted under 35 U.S.C. 154(b) by 771 days.

(21) Appl. No.: 12/495,668

(22) Filed: Jun. 30, 2009

(65) Prior Publication Data

US 2010/0327736 A1 Dec. 30, 2010

(51) Int. Cl.
*H01L 51/54* (2006.01)
*C09K 11/06* (2006.01)

(52) U.S. Cl.
USPC .... 428/690; 428/917; 313/504; 257/E51.044; 546/10; 548/101

(58) Field of Classification Search
None
See application file for complete search history.

(56) References Cited

U.S. PATENT DOCUMENTS

| | | | |
|---|---|---|---|
| 2002/0024293 A1 | 2/2002 | Igarashi et al. | |
| 2002/0034656 A1 | 3/2002 | Thompson et al. | |
| 2003/0017361 A1 | 1/2003 | Thompson et al. | |
| 2003/0059646 A1* | 3/2003 | Kamatani et al. | 428/690 |
| 2003/0068536 A1* | 4/2003 | Tsuboyama et al. | 428/704 |
| 2007/0085073 A1* | 4/2007 | Inoue et al. | 257/40 |
| 2007/0184303 A1* | 8/2007 | Byun et al. | 428/690 |

FOREIGN PATENT DOCUMENTS

| | | |
|---|---|---|
| EP | 1434286 A1 | 6/2004 |
| WO | WO 2005/049762 A1 * | 6/2005 |
| WO | 2006090301 A1 | 8/2006 |

* cited by examiner

*Primary Examiner* — Marie R. Yamnitzky
(74) *Attorney, Agent, or Firm* — Pai Patent & Trademark Law Firm; Chao-Chang David Pai

(57) ABSTRACT

A green phosphorescent iridium complex represented by Formula (I) is provided.

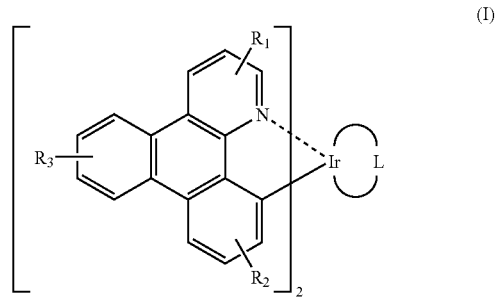

In Formula (I), R1, R2 and R3 are, independently, hydrogen, halogen, substituted or non-substituted C1-6 alkyl, C1-6 alkoxy, cycloalkyl, substituted or non-substituted aryl, amino or heteroaryl, and L is a heterocyclic ring containing N—N or N—O ligand. The invention also provides a method for fabricating the green phosphorescent iridium complex and an organic light-emitting diode including the green phosphorescent iridium complex.

12 Claims, No Drawings

GREEN PHOSPHORESCENT IRIDIUM COMPLEXES, FABRICATION METHOD THEREOF AND ORGANIC LIGHT-EMITTING DIODES COMPRISING THE SAME

BACKGROUND OF THE INVENTION

1. Field of the Invention

The invention relates to an organometallic complex, and more particularly to a green phosphorescent iridium complex applied in organic light-emitting diodes and fabrication method thereof.

2. Description of the Related Art

The first high efficiency organic electroluminescent device was developed by Kodak Corporation in 1987. Since then, organic (polymer) electroluminescent devices have been widely applied. Organic electroluminescent devices are applied in flat panel displays due to their high illumination, light weight, thin profile, self-illumination, low power consumption, wide viewing angle, simple fabrication methods and rapid response time. Additionally, when applying organic electroluminescent devices in flat panel displays, no backlight modules in the flat panel displays are required.

The theory of electroluminescence is described as follows. When an external electric field is applied to an organic semiconductor thin film device, electrons and holes are injected from a cathode and an anode, respectively, transported and then recombined to form excitons in an emitting layer. Energy is further transported from the excitons to luminescent molecules under a continuous electrical field. Finally, the luminescent molecules emit light converted from the energy. A common organic electroluminescent device structure comprises an ITO anode, a hole transport layer evaporated on the ITO anode, an emitting layer evaporated on the hole transport layer, a hole blocking layer evaporated on the emitting layer, an electron transport layer evaporated on the hole blocking layer, and a cathode evaporated on the electron transport layer. A multiple-layered organic electroluminescent device may further comprise a hole injection layer formed between the anode and the hole transport layer or an electron injection layer formed between the cathode and the electron transport layer evaporated from a proper organic material to improve carrier injection efficiency, thereby reducing driving voltage and increasing carrier recombination.

When luminescent molecules absorb energy to achieve an excited state, fluorescence or phosphorescence illumination is subsequently emitted. Fluorescence illumination is emitted via radiation transition from a singlet excited state to a ground state. Phosphorescence illumination is emitted via a radiation transition from a triplet excited state to the ground state. In a fluorescence electroluminescent device, 75% of the excitons form by recombination of electrons and holes to achieve a triplet excited state, the remaining 25% of the excitons do not form due to spin forbidden effects. Additionally, there is no illumination when the excitons transit from the triplet excited state to a ground state. Thus, a fluorescence electroluminescent device has only 25% internal quantum efficiency, which substantially limits its external quantum efficiency to lower than 5%. Accordingly, phosphorescent materials have been developed to fully utilize the characteristics of the triplet excited state transition to improve the internal quantum efficiency of electroluminescent devices from 25% to 100%. For example, red phosphorescent material is prepared by doping phosphorescent dyes in a host. Energy is transported from the host to the phosphorescent dyes through excitons for illumination. The most preferably dopant used is a phosphorescent dye containing heavy atoms. A heavy atom effect improves electron spin-spin coupling. With improved electron spin-spin coupling, the singlet state and triplet state are more effectively mixed and the probability of crossing between the singlet state and the triplet state is increased. Thus, the life span of the triplet excited state is reduced and the luminescent efficiency of the phosphorescent material is improved by four times that of the fluorescencent material.

Fac-Ir(ppy)$_3$ is a green phosphorescent material doped in a CBP host. A device utilizing fac-Ir(ppy)$_3$ can achieve a maximum external quantum efficiency of 8.0% (28 cd/A) and a luminescent efficiency of 31 lm/W and a maximum emitting wavelength of 510 nm and CIE of (0.27, 0.63). Specifically, the life span of the triplet excited state of fac-Ir(ppy)$_3$ is merely about 2 μs at room temperature, effectively reducing the saturation of devices under high current density. The structure of the fac-Ir(Ppy)$_3$ device has been further optimized by Watanabe et al. When a doping concentration of fac-Ir(ppy)$_3$ is 8.7% for a fac-Ir(ppy)$_3$ device, under an illumination of 100 cd/m$^2$, the fac-Ir(ppy)$_3$ device can achieve an external quantum efficiency of 14.9% and luminescent efficiency of 43.31 lm/W, which is about two times that of the original fac-Ir(ppy)$_3$ device. Meanwhile, (ppy)$_2$Ir(acac) is another green phosphorescent material commonly used. An ITO/HMTPD/(ppy)$_2$Ir(acac):TAZ/Alq/Mg:Ag device has a maximum emitting wavelength of 520 nm and CIE of (0.31, 0.64) and maximum external quantum efficiency of 19% due to improved control of balance between the electrons and holes and luminescent efficiency of 60 lm/W. Certainly, nearly 100% phosphorescent efficiency of (ppy)$_2$Ir(acac) is also an indispensable characteristic to prepare high-efficiency devices. A series of compounds which comprises iridium and a series of benzoimidazole-containing derivatives serving as ligands have optimal thermal stability. A yellow-green pbi$_2$Ir(acac) device has a maximum emitting wavelength of 530 nm, CIE of (0.36, 0.60), maximum quantum efficiency of 16.7% and maximum luminescent efficiency of 20 lm/W.

Other phosphorescent materials which comprise an iridium center and various ligands have been synthesized. The luminescent property effect, by the alternating of various ligands, such as emitting wavelength and luminescent efficiency has been disclosed, for example in EPO 1,434,286. In US 2002/024293, a blue phosphorescent iridium complex material with an emitting wavelength exceeding 500 nm is disclosed. The device has an external quantum efficiency exceeding 5%. In US 2002/034656 and 2003/017361, a platinum complex with various emitting wavelengths of 425 nm, 475 nm, 500 nm, 575 nm and 615 nm, ranging from blue light to orange-red light, is disclosed.

BRIEF SUMMARY OF THE INVENTION

One embodiment of the invention provides a green phosphorescent iridium complex represented by Formula (I):

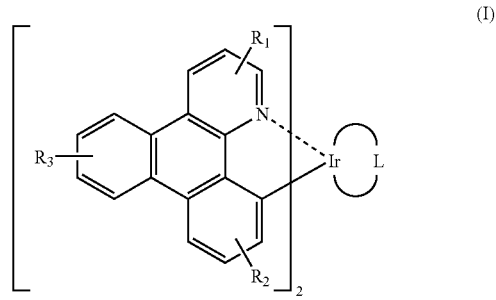

wherein R1, R2 and R3 are, independently, hydrogen, halogen, substituted or non-substituted C1-6 alkyl, C1-6 alkoxy, cycloalkyl, substituted or non-substituted aryl, amino or heteroaryl, and L is a heterocyclic ring containing N—N or N—O ligand.

One embodiment of the invention provides a method for fabricating a green phosphorescent iridium complex which comprises mixing a 9-phenanthrylamine derivative with a metal halide, slowly adding an acidic solvent, adding an α,β-unsaturated alkene aldehyde or a α,β-unsaturated alkene ketone to react and form a dibenzo[h,f]quinoline (DBQ) derivative, mixing the dibenzo[h,f]quinoline (DBQ) derivative with an iridium halide to react and form an iridium dimer complex, and mixing the iridium dimer complex with a compound containing acetylacetone or a heterocyclic ring containing N—N or N—O ligand to react and complete preparation of a green phosphorescent iridium complex represented by Formula (I):

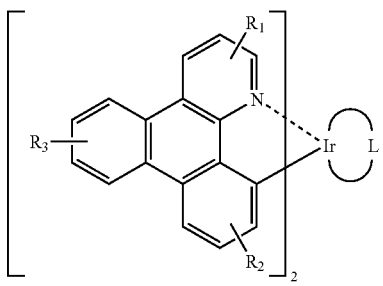

(I)

, wherein R1, R2 and R3 are, independently, hydrogen, halogen, substituted or non-substituted C1-6 alkyl, C1-6 alkoxy, cycloalkyl, substituted or non-substituted aryl, amino or heteroaryl, and L is a compound containing acetylacetone or a heterocyclic ring containing N—N or N—O ligand.

One embodiment of the invention provides an organic light-emitting diode comprising a cathode and an anode, and an emitting layer comprising the disclosed green phosphorescent iridium complex represented by Formula (I) disposed between the cathode and the anode.

A detailed description is given in the following embodiments.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

One embodiment of the invention provides a green phosphorescent iridium complex represented by Formula (I):

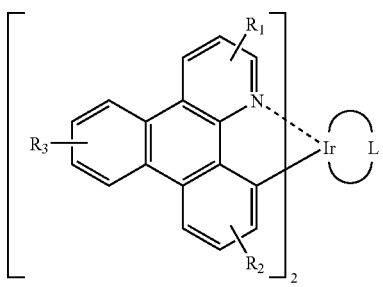

(I)

In Formula (I), R1, R2 and R3 may be, independently, hydrogen, halogen, substituted or non-substituted C1-6 alkyl, C1-6 alkoxy, cycloalkyl, substituted or non-substituted aryl, amino or heteroaryl, for example methyl, ethyl, cyclohexyl, trifluoromethyl, benzyl, phenyl, naphthyl, diphenyl, anthryl, pyrenyl, phenanthryl, benzofuranyl, thiophenyl, pyridine, quinoline, isoquinoline, pyrazine, pyrimidine, pyrrole, pyrazole, imidazole, indole, thiazole, isothiazole, oxazole, isoxazole, benzothiazole, benzoxazole or phenanthroline.

L may be a heterocyclic ring containing N—N or N—O ligand, for example:

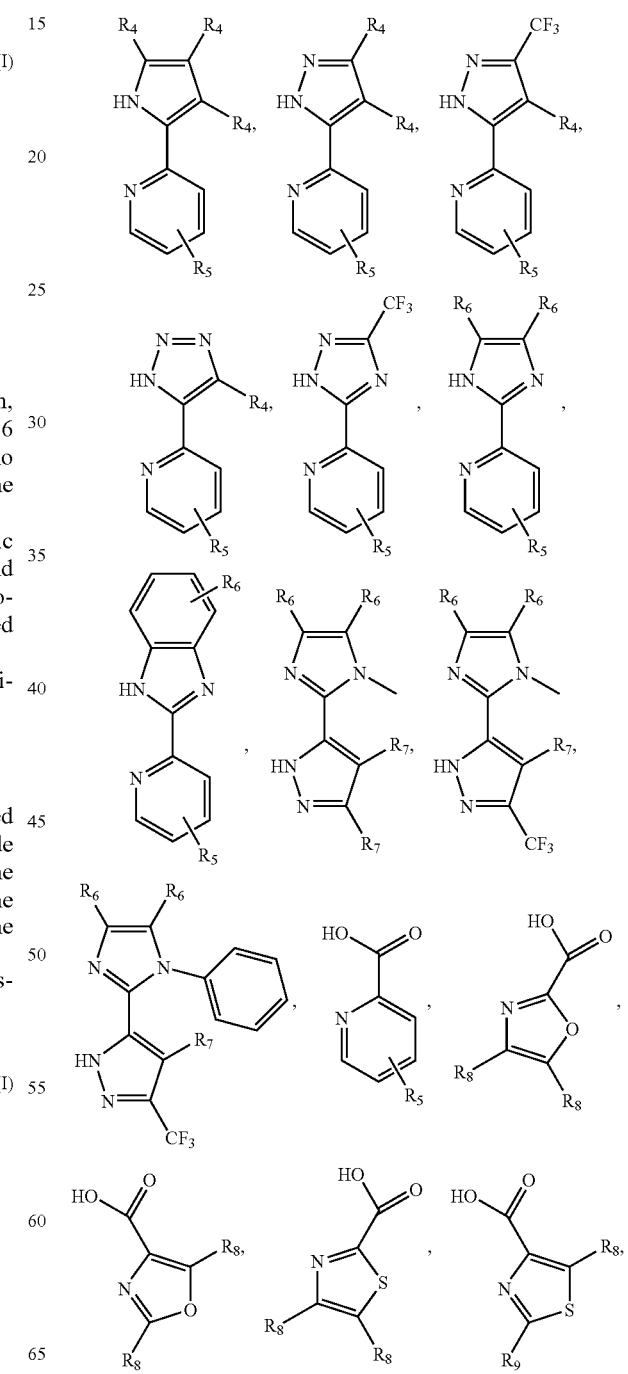

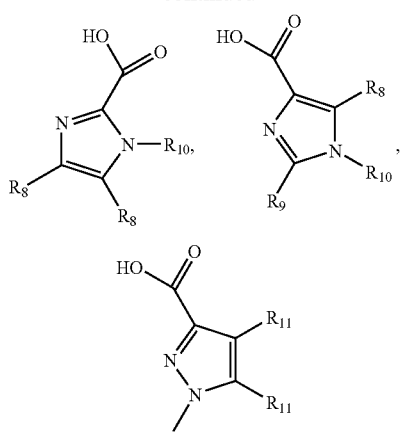

In the foregoing formulae, R4~R11 may be, independently, hydrogen, halogen, substituted or non-substituted C1-6 alkyl, C1-6 alkoxy, cycloalkyl, substituted or non-substituted aryl, amino or heteroaryl, for example methyl, ethyl, cyclohexyl, trifluoromethyl, benzyl, phenyl, naphthyl, diphenyl, anthryl, pyrenyl, phenanthryl, benzofuranyl, thiophenyl, pyridine, quinoline, isoquinoline, pyrazine, pyrimidine, pyrrole, pyrazole, imidazole, indole, thiazole, isothiazole, oxazole, isoxazole, benzothiazole, benzoxazole or phenanthroline.

Some specific green phosphorescent iridium complexes of the invention are disclosed herein and as follows:

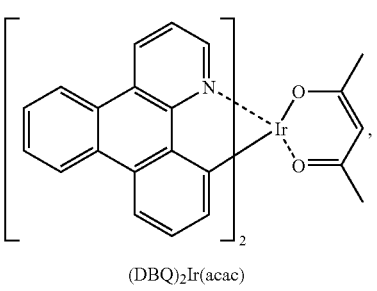

(DBQ)₂Ir(acac)

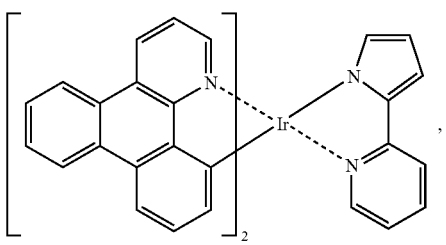

(DBQ)₂Ir(pp)

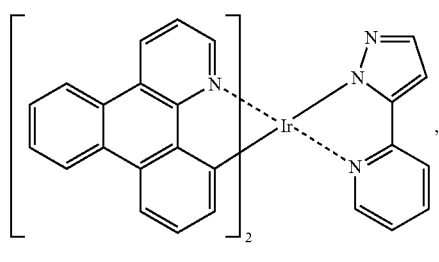

(DBQ)₂Ir(pzpy)

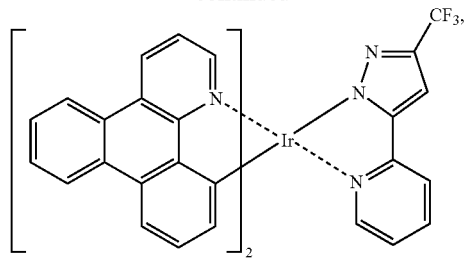

(DBQ)₂Ir(tfpzpy)

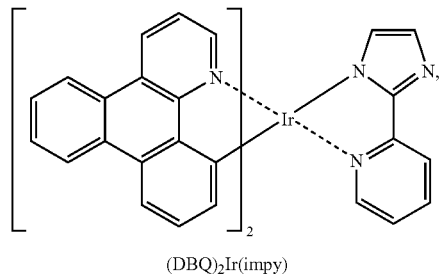

(DBQ)₂Ir(impy)

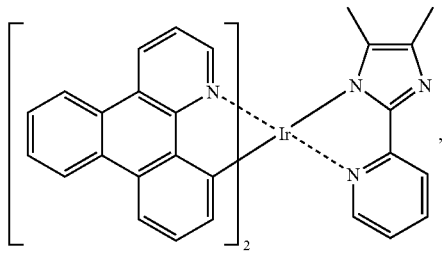

(DBQ)₂Ir(dmpyi)

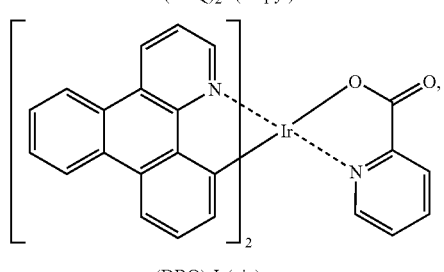

(DBQ)₂Ir(pic)

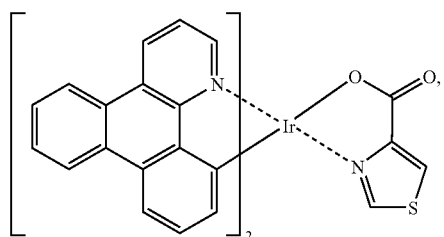

(DBQ)₂Ir(tac)

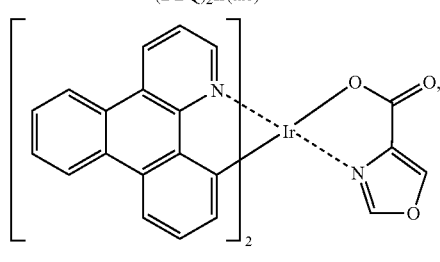

(DBQ)₂Ir(oac)

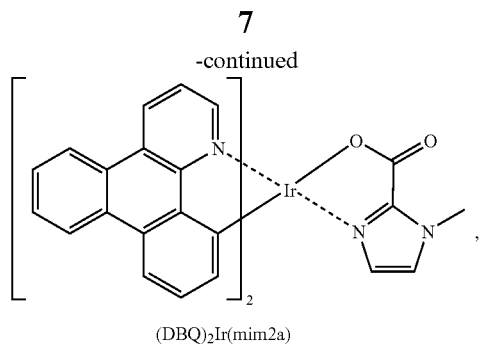
(DBQ)₂Ir(mim2a)
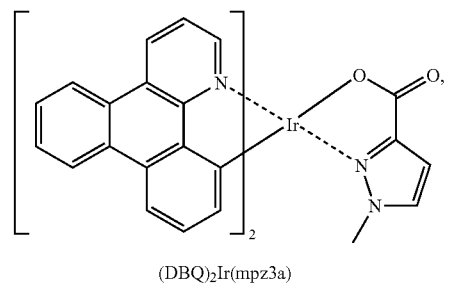
(DBQ)₂Ir(mpz3a)
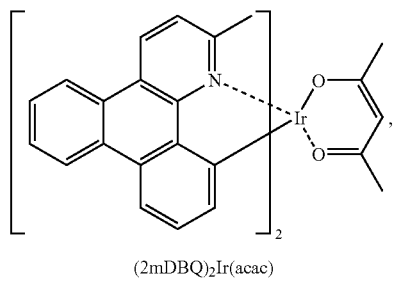
(2mDBQ)₂Ir(acac)
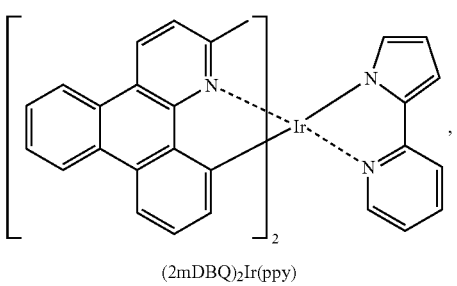
(2mDBQ)₂Ir(ppy)
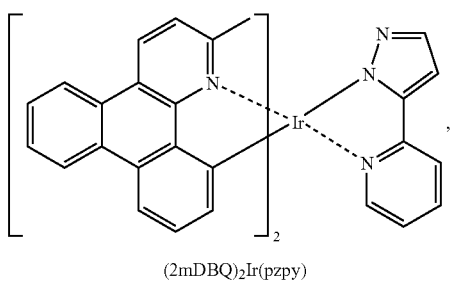
(2mDBQ)₂Ir(pzpy)
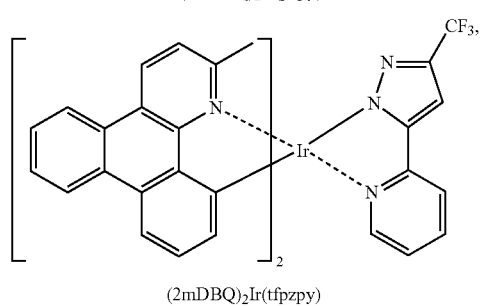
(2mDBQ)₂Ir(tfpzpy)
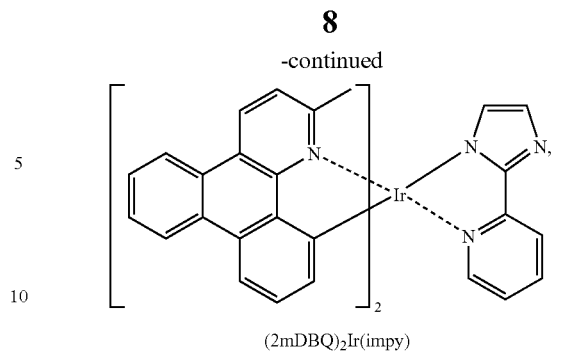
(2mDBQ)₂Ir(impy)
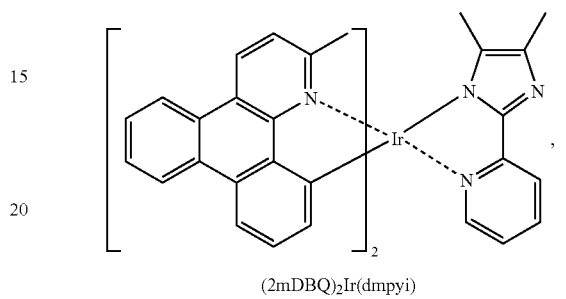
(2mDBQ)₂Ir(dmpyi)
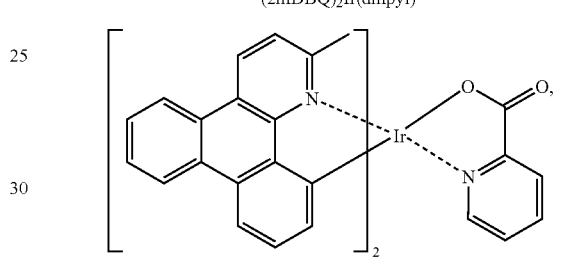
(2mDBQ)₂Ir(pic)
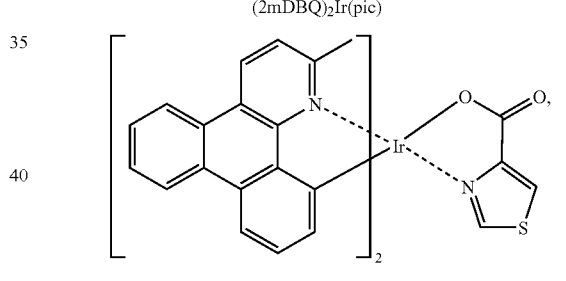
(2mDBQ)₂Ir(tac)
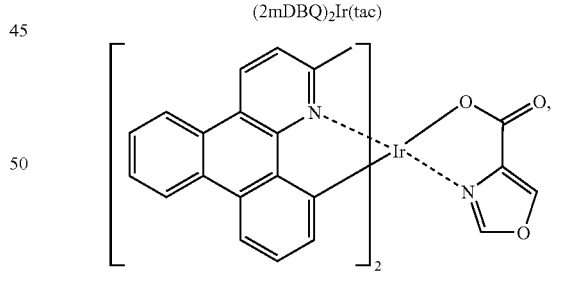
(2mDBQ)₂Ir(oac)
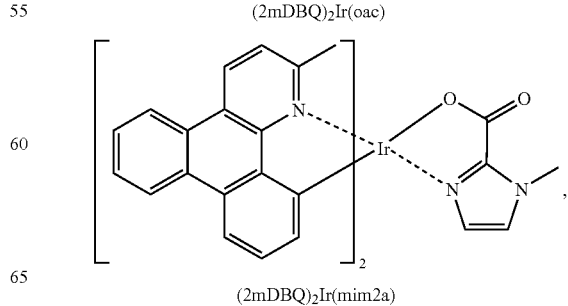
(2mDBQ)₂Ir(mim2a)

-continued
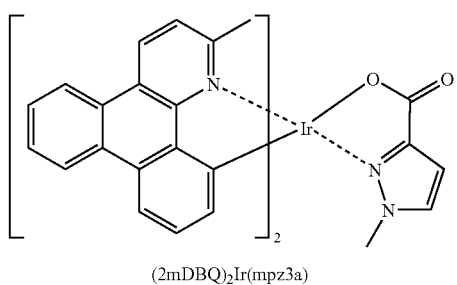
(2mDBQ)₂Ir(mpz3a)
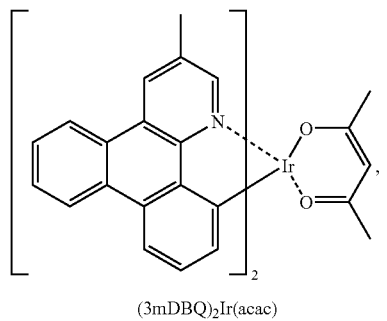
(3mDBQ)₂Ir(acac)
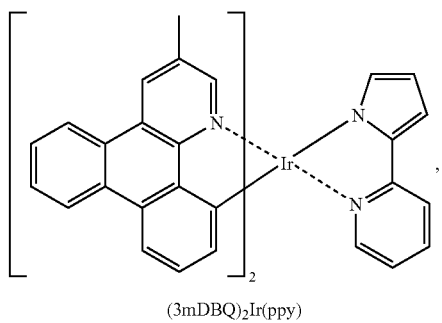
(3mDBQ)₂Ir(ppy)
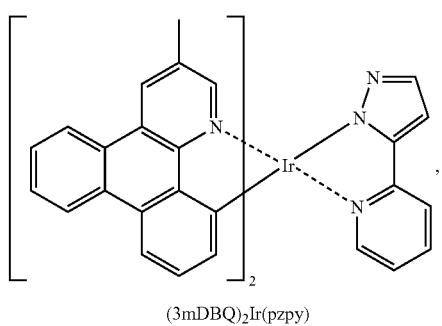
(3mDBQ)₂Ir(pzpy)
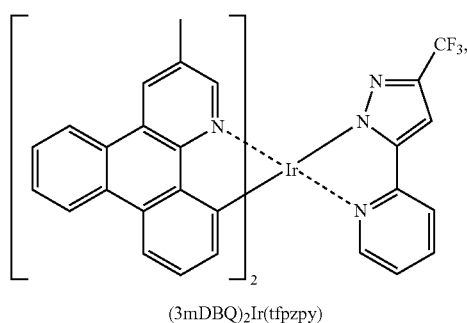
(3mDBQ)₂Ir(tfpzpy)
-continued
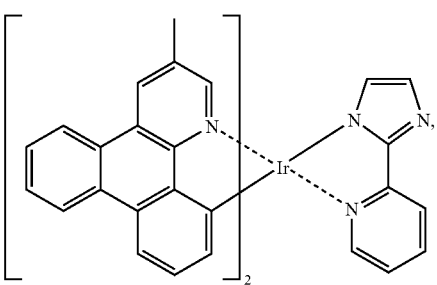
(3mDBQ)₂Ir(impy)
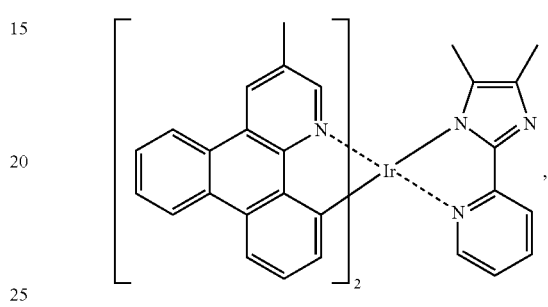
(3mDBQ)₂Ir(dmpyi)
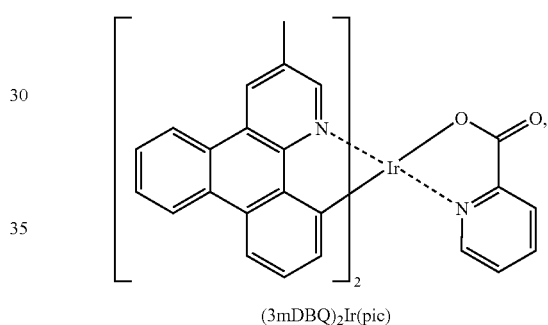
(3mDBQ)₂Ir(pic)
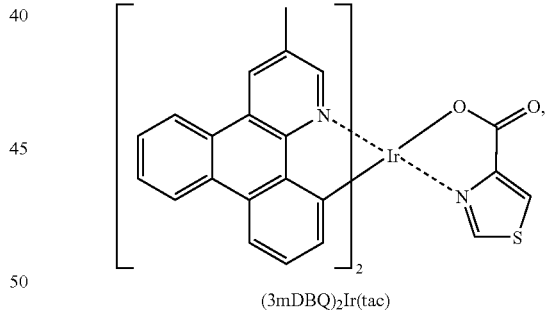
(3mDBQ)₂Ir(tac)
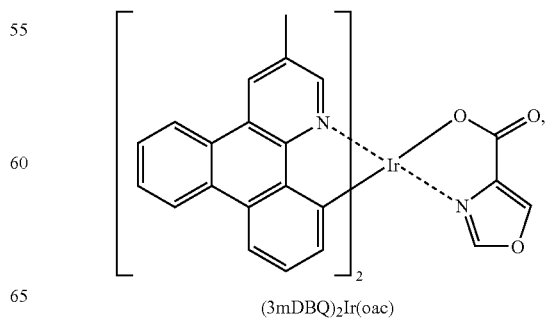
(3mDBQ)₂Ir(oac)

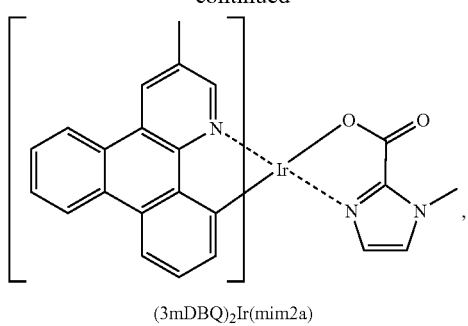
(3mDBQ)₂Ir(mim2a)
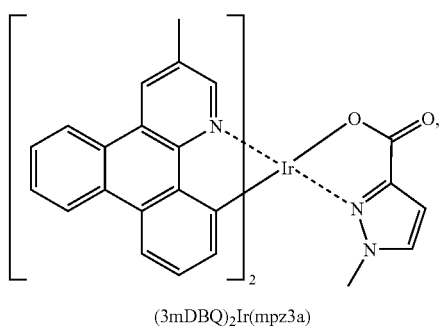
(3mDBQ)₂Ir(mpz3a)
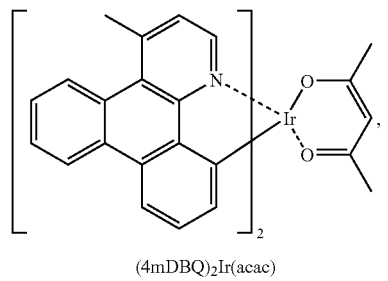
(4mDBQ)₂Ir(acac)
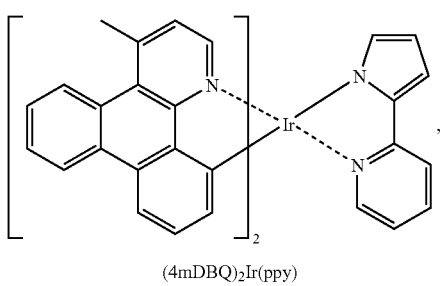
(4mDBQ)₂Ir(ppy)
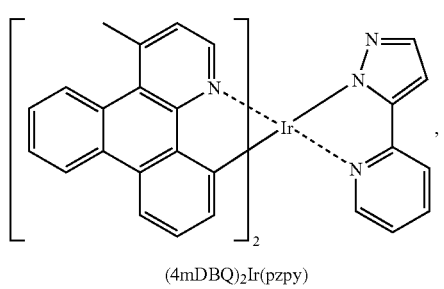
(4mDBQ)₂Ir(pzpy)
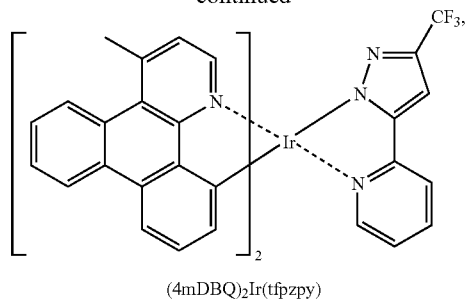
(4mDBQ)₂Ir(tfpzpy)
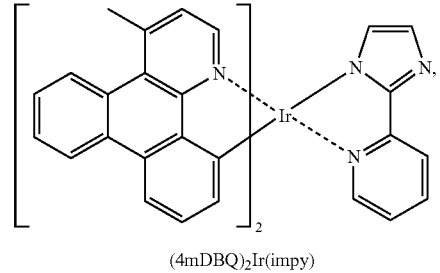
(4mDBQ)₂Ir(impy)
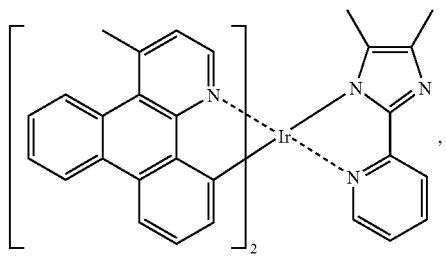
(4mDBQ)₂Ir(dmpyi)
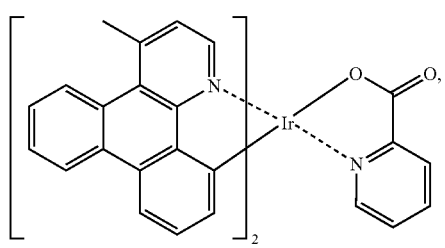
(4mDBQ)₂Ir(pic)
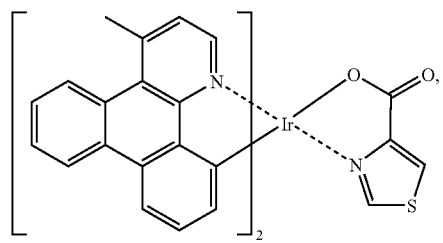
(4mDBQ)₂Ir(tac)
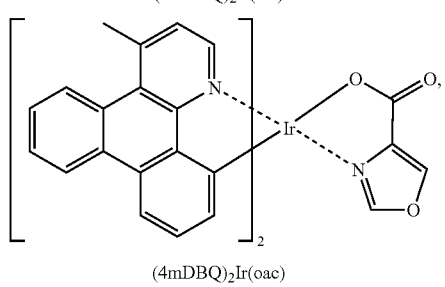
(4mDBQ)₂Ir(oac)

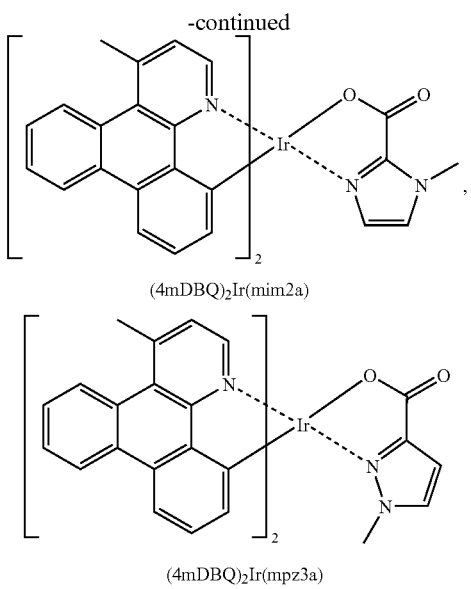

(4mDBQ)₂Ir(mim2a)

(4mDBQ)₂Ir(mpz3a)

One embodiment of the invention provides a method for fabricating a green phosphorescent iridium complex, which comprises the following steps. A 9-aminophenanthrene derivative and a metal halide are mixed. Next, an acidic solvent is slowly added. An α,β-unsaturated alkene aldehyde or a α,β-unsaturated alkene ketone is then added to react and form a dibenzo[h,f]quinoline (DBQ) derivative. Next, the dibenzo[h,f]quinoline (DBQ) derivative and an iridium halide are mixed to react and form an iridium dimer complex. The iridium dimer complex with a compound containing acetylacetone or a heterocyclic ring containing N—N or N—O ligand are then mixed to react and complete preparation of a green phosphorescent iridium complex represented by Formula (I):

(I)

The metal halide may comprise ferric chloride or zinc chloride. The acidic solvent may be acetic acid. The α,β-unsaturated alkene aldehyde may comprise propylene aldehyde or alkyl alkene aldehyde. The α,β-unsaturated alkene ketone may comprise methyl vinyl ketone. The iridium halide may comprise iridium chloride.

In Formula (I), R1, R2 and R3 may be, independently, hydrogen, halogen, substituted or non-substituted C1-6 alkyl, C1-6 alkoxy, cycloalkyl, substituted or non-substituted aryl, amino or heteroaryl, for example methyl, ethyl, cyclohexyl, trifluoromethyl, benzyl, phenyl, naphthyl, diphenyl, anthryl, pyrenyl, phenanthryl, benzofuranyl, thiophenyl, pyridine, quinoline, isoquinoline, pyrazine, pyrimidine, pyrrole, pyrazole, imidazole, indole, thiazole, isothiazole, oxazole, isoxazole, benzothiazole, benzoxazole or phenanthroline.

L may be a heterocyclic ring containing N—N or N—O ligand, for example:

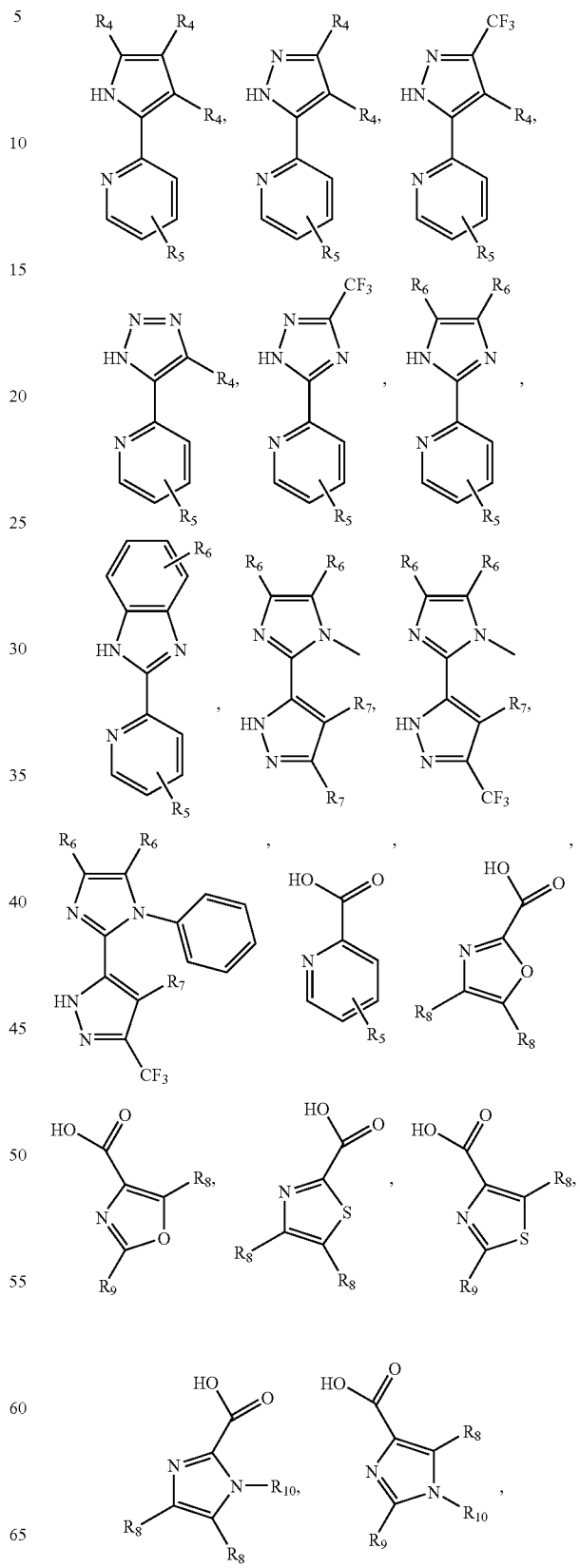

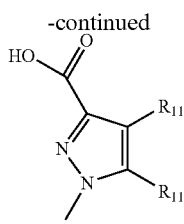

In the foregoing formulae, R4~R11 may be, independently, hydrogen, halogen, substituted or non-substituted C1-6 alkyl, C1-6 alkoxy, cycloalkyl, substituted or non-substituted aryl, amino or heteroaryl, for example methyl, ethyl, cyclohexyl, trifluoromethyl, benzyl, phenyl, naphthyl, diphenyl, anthryl, pyrenyl, phenanthryl, benzofuranyl, thiophenyl, pyridine, quinoline, isoquinoline, pyrazine, pyrimidine, pyrrole, pyrazole, imidazole, indole, thiazole, isothiazole, oxazole, isoxazole, benzothiazole, benzoxazole or phenanthroline.

One embodiment of the invention provides an organic light-emitting diode comprising a cathode and an anode, and an emitting layer comprising the disclosed green phosphorescent iridium complex represented by Formula (I) disposed between the cathode and the anode.

The organic light-emitting diode of the invention emits blue-green to yellow-green phosphorescence, with an illumination of about $1 \times 10^3$-$1 \times 10^6$ cd/m$^2$, a luminescent efficiency of about 1-150 lm/W, a wavelength of about 480-550 nm, a CIE of (0.30, 0.65), and an external quantum efficiency of about 1-30%.

EXAMPLES

Example 1

Synthesis of dibenzo[h,f]quinoline [DBQ]

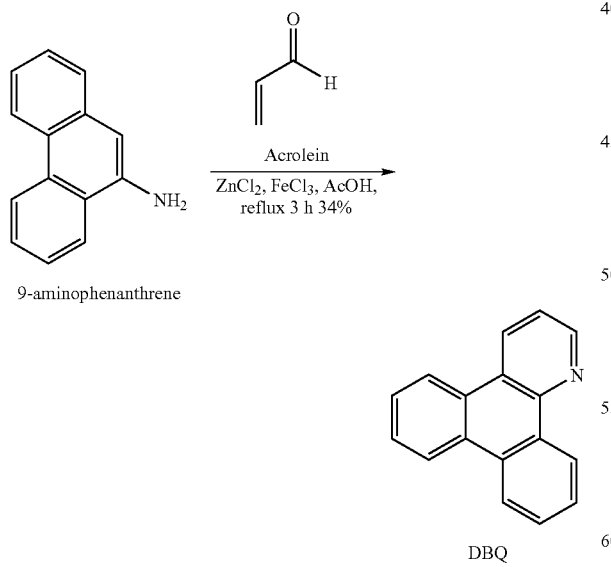

2.52 g of 9-aminophenanthrene (13 mmol) was added into a two-necked bottle and placed in a drying oven. After 2.1 g of ferric chloride (13 mmol) and 1.77 g of zinc chloride (13 mmol) were added, a nitrogen gas was conducted. Next, 25 ml of acetic acid was slowly added. Next, 875 mg of propenal (15.6 mmol) was then added with thermal reflux for three hours. After cooling, 15% of the NaOH aqueous solution was slowly added under an ice bath to neutralize the pH level to 7. Next, the resulting solution was extracted by adding ethyl acetate and a saturated NaHCO$_3$ aqueous solution. Following, water was removed by adding dried magnesium sulfate and solvent was removed by using filtration and concentration processes. The result was next purified using column chromatography using n-hexane/ethyl acetate (4:1) as an eluent. 1.0 g of a white dibenzo[h,f]quinoline (DBQ) solid was obtained, with a yield of 34%.

$^1$H NMR (400 MHz; CDCl$_3$): δ9.31 (m, 1H), 8.94 (dd, J=4.4, 1.6 Hz, 1H), 8.79 (dd, J=8.4, 1.6 Hz, 1H), 8.62 (dd, J=7.6, 2.0 Hz, 1H), 8.60-8.55 (m, 1H), 8.50 (dd, J=7.6, 2.0 Hz, 1H), 7.77-7.69 (m, 2H), 7.69-7.59 (m, 2H), 7.52 (dd, J=8.0, 4.0 Hz, 1H). HRMS (EI, m/z): calcd for C$_{17}$H$_{11}$N 229.0891. found 229.0890 (M$^+$).

Example 2

Synthesis of 2-methyl(dibenzo[h,f]quinoline) [2 mDBQ] and 4-methyl(dibenzo[h,f]quinoline) [4 mDBQ]

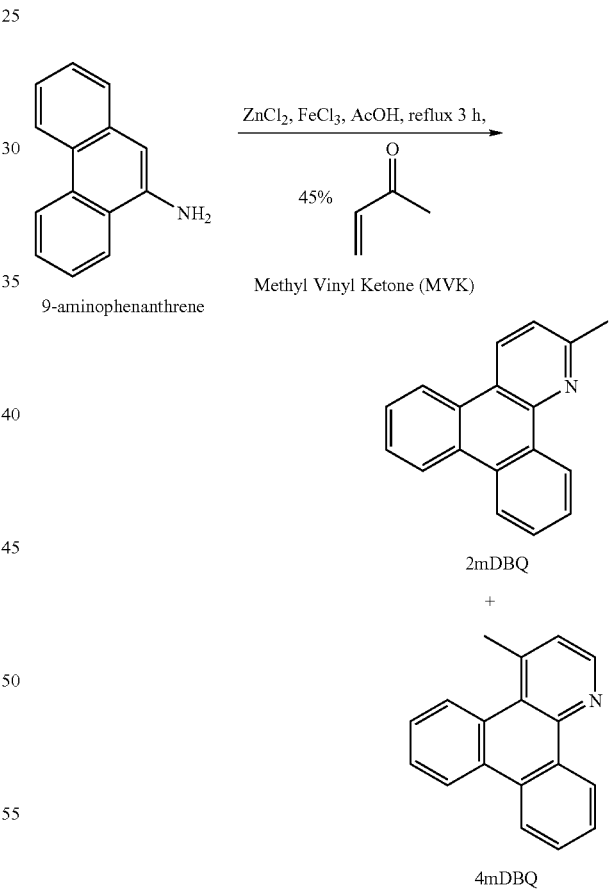

2.2 g of 9-aminophenanthrene (11.4 mmol) was added into a two-necked bottle and placed in a drying oven. After 1.85 g of ferric chloride (11.4 mmol) and 1.55 g of zinc chloride (11.4 mmol) were added, a nitrogen gas was conducted. Next, 20 ml of acetic acid was slowly added. 876 mg of methyl vinyl acetone (12.5 mmol) was then added with thermal reflux for three hours. After cooling, 15% of the NaOH aqueous solution was slowly added under an ice bath to neutralize the pH level to 7. Next, the resulting solution was extracted by adding ethyl acetate and a saturated NaHCO$_3$ aqueous solution. Following, water was removed by adding dried magnesium sulfate and solvent was removed by using filtration and concentration processes. The result was next purified using column chromatography using n-hexane/ethyl acetate (4:1) as an eluent. 1.25 g of a white solid of 2-methyl dibenzo[h,f]quinoline (2 mDBQ) and 4-methyl dibenzo[h,f]quinoline (4 mDBQ) isomers was obtained, with a yield of 45%.

[2 mDBQ] $^1$H NMR (400 MHz; CDCl$_3$): δ9.40-9.34 (m, 1H), 8.74 (d, J=8.4 Hz, 1H), 8.68-8.63 (m, 1H), 8.63-8.58 (m, 1H), 8.56-8.50 (m, 1H), 7.76-7.68 (m, 1H), 7.68-7.62 (m, 1H), 7.72 (d, J=8.4 Hz, 1H), 2.81 (s, 3H). HRMS (EI, m/z): calcd for C$_{18}$H$_{13}$N 243.1048. found 243.1051 (M$^+$).

[4 mDBQ] $^1$H NMR (400 MHz; CDCl$_3$): δ9.35-9.28 (m, 1H), 8.74 (d, J=4.4 Hz, 1H), 8.63 (dd, J=8.0, 1.2 Hz, 1H), 8.55-8.49 (m, 1H), 7.72-7.66 (m, 2H), 7.63 (ddd, J=7.6, 1.2 Hz, 1H), 7.56 (ddd, J=7.6, 1.2 Hz, 1H), 7.30 (dd, J=4.8, 0.8 Hz, 1H), 2.98 (s, 3H). HRMS (EI, m/z): calcd for C$_{18}$H$_{13}$N 243.1048. found 243.1050 (M$^+$).

Example 3

Synthesis of 3-methyl(dibenzo[h,f]quinoline) [3 mDBQ]

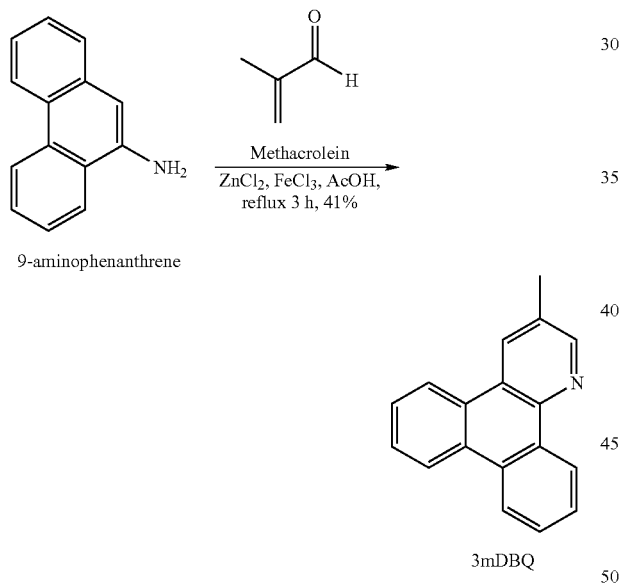

1.58 g of 9-aminophenanthrene (8.2 mmol) was added into a two-necked bottle and placed in a drying oven. After 1.33 g of ferric chloride (8.2 mmol) and 1.12 g of zinc chloride (8.2 mmol) were added, a nitrogen gas was conducted. Next, 18 ml of acetic acid was slowly added. 690 mg of methyl propenal (9.8 mmol) was then added with thermal reflux for three hours. After cooling, 15% of the NaOH aqueous solution was slowly added under an ice bath to neutralize the pH level to 7. Next, the resulting solution was extracted by adding ethyl acetate and a saturated NaHCO$_3$ aqueous solution. Following, water was removed by adding dried magnesium sulfate and solvent was removed by using filtration and concentration processes. The result was next purified using column chromatography using n-hexane/ethyl acetate (4:1) as an eluent. 817 mg of a white 3-methyl dibenzo[h,f]quinoline (3 mDBQ) solid was obtained, with a yield of 41%.

$^1$H NMR (400 MHz; CDCl$_3$): δ9.30-9.22 (m, 1H), 8.76 (d, J=4.0 Hz, 1H), 8.61 (dd, J=7.6, 1.6 Hz, 1H), 8.59-8.53 (m, 2H), 8.49 (dd, J=7.6, 1.6 Hz, 1H), 7.74-7.67 (m, 2H), 7.67-7.58 (m, 2H), 2.55 (s, 3H). HRMS (EI, m/z): calcd for C$_{18}$H$_{13}$N 243.1048. found 243.1055 (M$^+$).

Example 4

Synthesis of Bis(3-methyl(dibenzo[h,f]quinolinato)-N,C$^{2'}$)iridium(III) (thiazole-4-carboxylic acid) [(3 mDBQ)$_2$Ir(tac)]

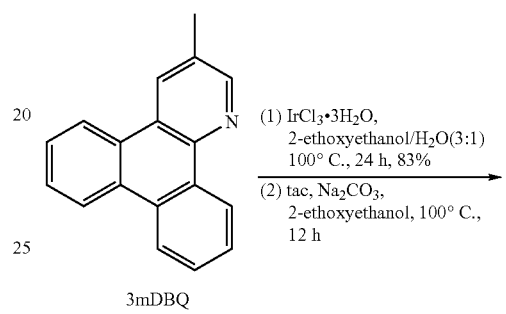

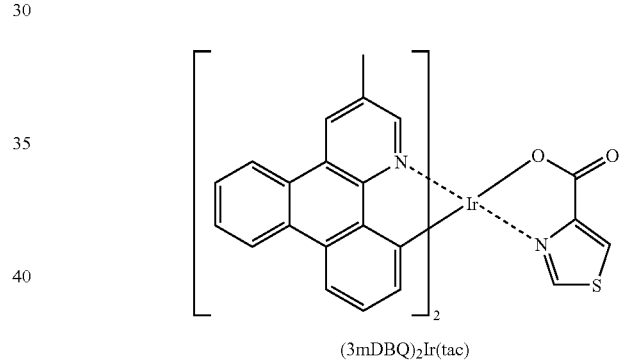

1.14 g of 3 mDBQ (4.68 mmol) and 750 mg of IrCl$_3$.nH$_2$O (2.13 mmol, dissolved in 2-ethoxyethanol/water (3:1)) were mixed in a reaction bottle and heated to 100° C. After reaction for 24 hours, a filtered solid was collected and washed by water, n-hexane and ether for several times. After drying, 1.25 g of a yellow iridium dimer complex solid was obtained, with a yield of 83%. 100 mg of an iridium dimer complex (0.07 mmol), 37.2 mg of Na$_2$CO$_3$ (0.351 mmol), 27.2 mg of thiazole-4-carboxylic acid (0.211 mmol) and 1 ml of 2-ethoxyethanol were mixed in a reaction bottle and heated to 100° C. for 12 hours. After cooling, a filtered solid was collected and washed by water and n-hexane for several times. The results were purified using column chromatography using dichloromethane/methanol as an eluent. 88 mg of a yellow solid was obtained, with a yield of 78%.

$^1$H NMR (400 MHz; CDCl$_3$): δ9.03 (s, 1H), 8.68 (s, 1H), 8.66 (s, 1H), 8.62-8.53 (m, 5H), 8.19 (d, J=2.4 Hz, 1H), 8.06 (d, J=2.4 Hz, 1H), 7.92 (d, J=8.0 Hz, 1H), 7.89 (d, J=8.0 Hz, 1H), 7.70-7.64 (m, 4H), 7.01 (t, J=7.6 Hz, 1H), 6.99 (t, J=7.6 Hz, 1H), 6.44 (d, J=7.2 Hz, 1H), 6.28 (d, J=7.4 Hz, 1H), 2.68 (s, 3H), 2.51 (s, 3H).

Example 5

Synthesis of Bis(3-methyl(dibenzo[h,f]quinolinato)-N,C²')iridium(III) (1-methyl-1H-pyrazole-3-carboxylic acid) [(3 mDBQ)₂Ir(mpz3a)]

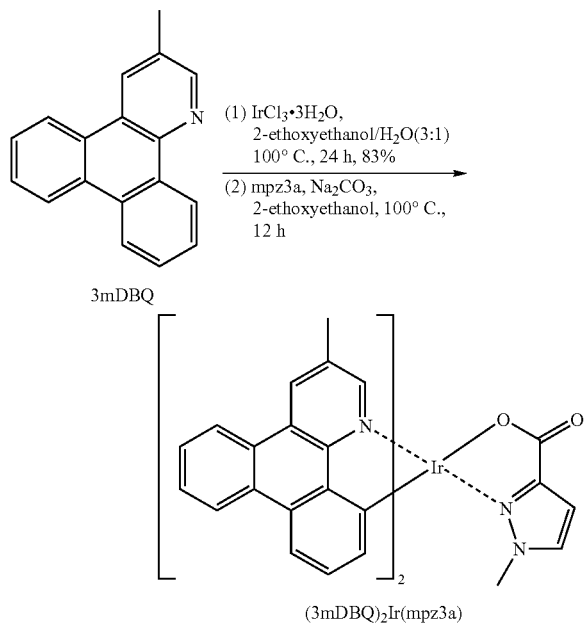

1.14 g of 3 mDBQ (4.68 mmol) and 750 mg of IrCl₃·nH₂O (2.13 mmol, dissolved in 2-ethoxyethanol/water (3:1)) were mixed in a reaction bottle and heated to 100° C. After reaction for 24 hours, a filtered solid was collected and washed by water, n-hexane and ether for several times. After drying, 1.25 g of a yellow iridium dimer complex solid was obtained, with a yield of 83%. 100 mg of an iridium dimer complex (0.07 mmol), 37.2 mg of Na₂CO₃ (0.351 mmol), 26.5 mg of 1-methyl-1H-pyrazole-3-carboxylic acid (0.211 mmol) and 1 ml of 2-ethoxyethanol were mixed in a reaction bottle and heated to 100° C. for 12 hours. After cooling, a filtered solid was collected and washed by water and n-hexane for several times. The results were purified using column chromatography using dichloromethane/methanol as an eluent. 90 mg of a yellow solid was obtained, with a yield of 80%.

$^1$H NMR (400 MHz; CDCl₃): δ9.03 (s, 1H), 8.67 (s, 2H), 8.64-8.51 (m, 5H), 7.88 (d, J=7.6 Hz, 1H), 7.86 (d, J=7.6 Hz, 1H), 7.70-7.62 (m, 4H), 7.25 (d, J=2.4 Hz, 1H), 6.96 (t, J=7.6 Hz, 1H), 6.94 (t, J=7.6 Hz, 1H), 6.85 (d, J=2.4 Hz, 1H), 6.43 (d, J=7.2 Hz, 1H), 6.14 (d, J=7.2 Hz, 1H), 3.00 (s, 3H), 2.68 (s, 3H), 2.52 (s, 3H).

Example 6

Synthesis of Bis(3-methyl(dibenzo[h,f]quinolinato)-N,C²')iridium(III) (2-(1H-imidazol-2-yl)pyridine) [(3 mDBQ)₂Ir(impy)]

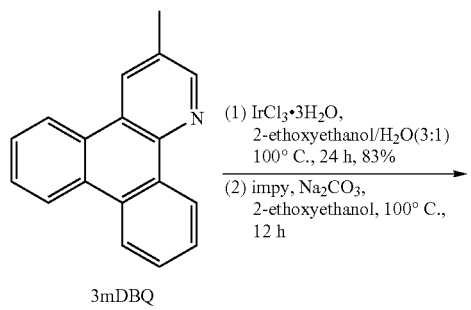

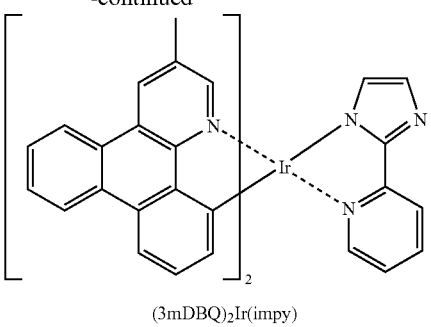

1.14 g of 3 mDBQ (4.68 mmol) and 750 mg of IrCl₃·nH₂O (2.13 mmol, dissolved in 2-ethoxyethanol/water (3:1)) were mixed in a reaction bottle and heated to 100° C. After reaction for 24 hours, a filtered solid was collected and washed by water, n-hexane and ether for several times. After drying, 1.25 g of a yellow iridium dimer complex solid was obtained, with a yield of 83%. 100 mg of an iridium dimer complex (0.07 mmol), 37.2 mg of Na₂CO₃ (0.351 mmol), 30.6 mg of 2-(1H-imidazol-2-yl)pyridine (0.211 mmol) and 1 ml of 2-ethoxyethanol were mixed in a reaction bottle and heated to 100° C. for 12 hours. After cooling, a filtered solid was collected and washed by water and n-hexane for several times. The results were purified using column chromatography using dichloromethane/methanol as an eluent. 89 mg of a yellow solid was obtained, with a yield of 78%.

$^1$H NMR (400 MHz; CDCl₃): δ 9.40 (s, 1H), 8.66 (s, 2H), 8.61-8.58 (m, 4H), 8.03 (d, J=8.0 Hz, 1H), 7.99 (d, J=8.0 Hz, 1H), 7.94 (t, J=7.8 Hz, 1H), 7.85 (s, 1H), 7.77 (d, J=5.6 Hz, 1H), 7.74-7.64 (m, 4H), 7.63 (s, 1H), 7.29 (s, 1H), 7.14 (t, J=7.2 Hz, 1H), 7.09 (t, J=7.2 Hz, 1H), 7.07 (t, J=7.2 Hz, 1H), 6.47 (s, 1H), 6.45 (d, J=7.6 Hz, 1H), 6.37 (d, J=7.6 Hz, 1H), 2.53 (s, 3H), 2.48 (s, 3H).

Example 7

Synthesis of Bis(3-methyl(dibenzo[h,f]quinolinato)-N,C²')iridium(III) (2-(4,5-dimethyl-1H-imidazol-2-yl)pyridine) [(3 mDBQ)₂Ir(dmpyi)]

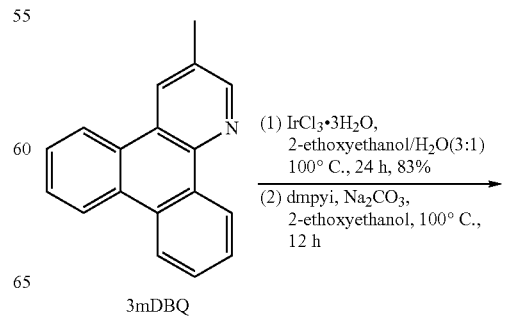

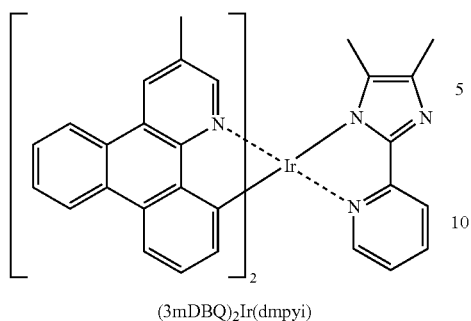

(3mDBQ)₂Ir(dmpyi)

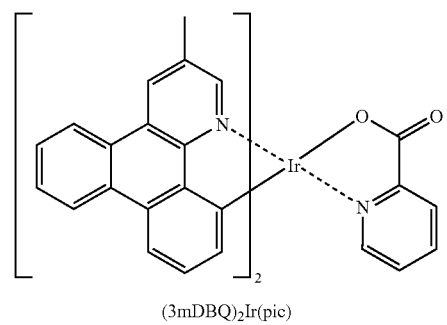

(3mDBQ)₂Ir(pic)

1.14 g of 3 mDBQ (4.68 mmol) and 750 mg of IrCl₃.nH₂O (2.13 mmol, dissolved in 2-ethoxyethanol/water (3:1)) were mixed in a reaction bottle and heated to 100° C. After reaction for 24 hours, a filtered solid was collected and washed by water, n-hexane and ether for several times. After drying, 1.25 g of a yellow iridium dimer complex solid was obtained, with a yield of 83%. 100 mg of an iridium dimer complex (0.07 mmol), 37.2 mg of Na₂CO₃ (0.351 mmol), 36.5 mg of 2-(4,5-dimethyl-1H-imidazol-2-yl)pyridine (0.211 mmol) and 1 ml of 2-ethoxyethanol were mixed in a reaction bottle and heated to 100° C. for 12 hours. After cooling, a filtered solid was collected and washed by water and n-hexane for several times. The results were purified using column chromatography using dichloromethane/methanol as an eluent. 89 mg of a yellow solid was obtained, with a yield of 75%.

¹H NMR (400 MHz; CDCl₃): δ 9.23 (d, J=7.2 Hz, 1H), 8.67 (s, 2H), 8.61-8.56 (m, 4H), 8.02 (d, J=8.0 Hz, 1H), 7.98 (s, 1H), 7.96 (d, J=8.0 Hz, 1H), 7.86 (t, J=7.6 Hz, 1H), 7.74-7.64 (m, 5H), 7.59 (s, 1H), 7.11 (t, J=7.6 Hz, 1H), 7.04 (t, J=7.6 Hz), 1H), 6.95 (t, J=6.4 Hz, 1H), 6.34 (m, 2H), 2.57 (s, 3H), 2.49 (s, 3H), 2.27 (s, 3H), 1.18 (s, 3H).

1.14 g of 3 mDBQ (4.68 mmol) and 750 mg of IrCl₃.nH₂O (2.13 mmol, dissolved in 2-ethoxyethanol/water (3:1)) were mixed in a reaction bottle and heated to 100° C. After reaction for 24 hours, a filtered solid was collected and washed by water, n-hexane and ether for several times. After drying, 1.25 g of a yellow iridium dimer complex solid was obtained, with a yield of 83%. 100 mg of an iridium dimer complex (0.07 mmol), 37.2 mg of Na₂CO₃ (0.351 mmol), 25.9 mg of picolinic acid (0.211 mmol) and 1 ml of 2-ethoxyethanol were mixed in a reaction bottle and heated to 100° C. for 12 hours. After cooling, a filtered solid was collected and washed by water and n-hexane for several times. The results were purified using column chromatography using dichloromethane/methanol as an eluent. 65 mg of a yellow solid was obtained, with a yield of 58%.

¹H NMR (400 MHz; CDCl₃) δ 8.95 (s, 1H), 8.65-8.53 (m, 6H), 8.36 (d, J=7.6 Hz, 1H), 7.95 (d, J=8.0 Hz, 1H), 7.89 (d, J=8.0 Hz, 1H), 7.86 (t, J=8.0 Hz, 1H), 7.78 (d, J=4.8 Hz, 1H), 7.70-7.52 (m, 4H), 7.43 (s, 1H), 7.04 (t, J=7.6 Hz, 1H), 6.98 (t, J=7.6 Hz, 1H), 6.44 (d, J=7.2 Hz, 1H), 6.27 (d, J=7.2 Hz, 1H), 2.64 (s, 3H), 2.44 (s, 3H).

Example 8

Synthesis of Bis(3-methyl(dibenzo[h,f]quinolinato)-N,C²')iridium(III) (picolinic acid) [(3 mDBQ)₂Ir(pic)]

Example 9

Synthesis of Bis(3-methyl(dibenzo[h,f]quinolinato)-N,C²')iridium(III) (oxazole-4-carboxylic acid) [(3 mDBQ)₂Ir(oac)]

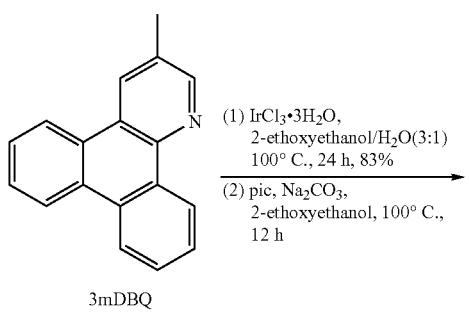

3mDBQ (1) IrCl₃•3H₂O, 2-ethoxyethanol/H₂O(3:1) 100° C., 24 h, 83%
(2) pic, Na₂CO₃, 2-ethoxyethanol, 100° C., 12 h

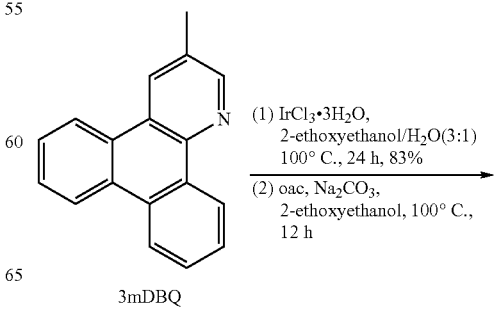

3mDBQ (1) IrCl₃•3H₂O, 2-ethoxyethanol/H₂O(3:1) 100° C., 24 h, 83%
(2) oac, Na₂CO₃, 2-ethoxyethanol, 100° C., 12 h

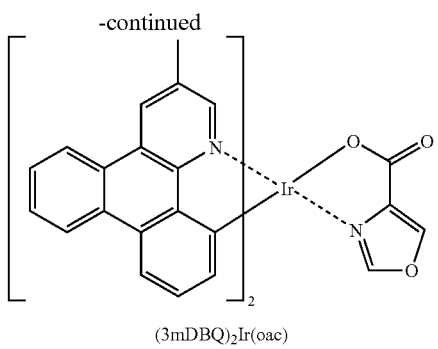

(3mDBQ)₂Ir(oac)

1.14 g of 3 mDBQ (4.68 mmol) and 750 mg of IrCl₃.nH₂O (2.13 mmol, dissolved in 2-ethoxyethanol/water (3:1)) were mixed in a reaction bottle and heated to 100° C. After reaction for 24 hours, a filtered solid was collected and washed by water, n-hexane and ether for several times. After drying, 1.25 g of a yellow iridium dimer complex solid was obtained, with a yield of 83%. 1 mg of an iridium dimer complex (0.07 mmol), 37.2 mg of Na₂CO₃ (0.351 mmol), 23.8 mg of oxazole-4-carboxylic acid (0.211 mmol) and 1 ml of 2-ethoxyethanol were mixed in a reaction bottle and heated to 100° C. for 12 hours. After cooling, a filtered solid was collected and washed by water and n-hexane for several times. The results were purified using column chromatography using dichloromethane/methanol as an eluent. 73 mg of a yellow solid was obtained, with a yield of 66%.

¹H NMR (400 MHz; CDCl₃): δ 9.00 (s, 1H), 8.71 (s, 1H), 8.68 (s, 1H), 8.63-8.53 (m, 4H), 8.22 (s, 1H), 8.03 (s, 1H), 7.89 (m, 2H), 7.69-7.64 (m, 4H), 7.58 (s, 1H), 6.98 (t, J=7.4 Hz, 2H), 6.42 (d, J=7.4 Hz, 1H), 6.24 (d, J=7.4 Hz, 1H), 2.69 (s, 3H), 2.58 (s, 3H).

Example 10

Synthesis of Bis(4-methyl(dibenzo[h,f]quinolinato)-N,C²')iridium (picolinic acid) [(4 mDBQ)₂Ir(pic)]

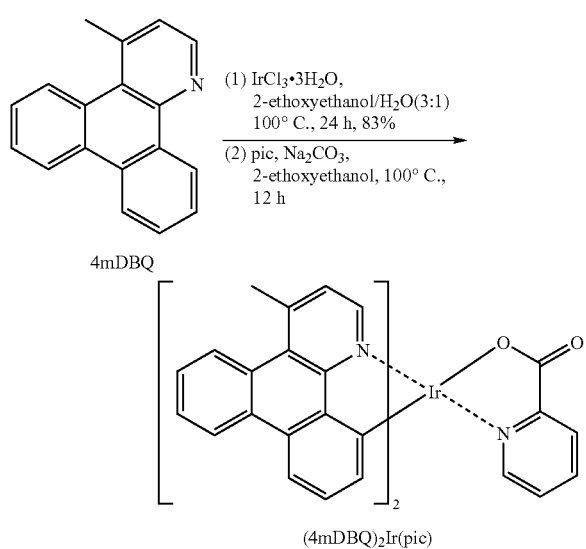

(4mDBQ)₂Ir(pic)

1.15 g of 4 mDBQ (4.73 mmol) and 758 mg of IrCl₃.nH₂O (2.15 mmol, dissolved in 2-ethoxyethanol/water (3:1)) were mixed in a reaction bottle and heated to 100° C. After reaction for 24 hours, a filtered solid was collected and washed by water, n-hexane and ether for several times. After drying, 1.4 g of a yellow iridium dimer complex solid was obtained, with a yield of 95%. 100 mg of an iridium dimer complex (0.07 mmol), 37.2 mg of Na₂CO₃ (0.351 mmol), 25.9 mg of picolinic acid (0.211 mmol) and 1 ml of 2-ethoxyethanol were mixed in a reaction bottle and heated to 100° C. for 12 hours. After cooling, a filtered solid was collected and washed by water and n-hexane for several times. The results were purified using column chromatography using dichloromethane/methanol as an eluent. 78 mg of a yellow solid was obtained, with a yield of 70%.

¹H NMR (400 MHz; CDCl₃): δ 8.97 (d, J=5.6 Hz, 1H), 8.77 (d, J=8.4 Hz, 1H), 8.73 (d, J=8.4 Hz, 1H), 8.67 (d, J=8.0 Hz, 1H), 8.60 (d, J=8.0 Hz, 1H), 8.32 (d, J=8.0 Hz, 1H), 7.96 (d, J=8.0 Hz, 1H), 7.90 (d, J=8.0 Hz, 1H), 7.82 (t, J=7.6 Hz, 1 H), 7.75 (d, J=4.8 Hz, 1H), 7.72-7.59 (m, 5H), 7.38 (d, J=5.6 Hz, 1H), 7.19 (t, J=7.6 Hz, 1H), 7.16 (d, J=5.6 Hz, 1H), 7.05 (t, J=7.8 Hz, 1H), 6.99 (t, J=7.8 Hz, 1H), 6.50 (d, J=7.2 Hz, 1H), 6.28 (d, J=7.2 Hz, 1H), 3.24 (s, 3H), 3.22 (s, 3H).

Example 11

Fabrication of an Organic Light-Emitting Diode

First, an ITO glass substrate was provided to serve as an anode and washed with a cleaning agent and deionized water. After drying, 4,4'-bis[N-(naphthyl)-N-phenyl-amino] biphenyl (NPB) and TCTA (4,4',4"-tris(N-carbazolyl)triphenylamine) were evaporated on the ITO glass substrate to form a hole transport layer. The disclosed green phosphorescent iridium complex and 4,4'-N,N'-dicarbazole-biphenyl (CBP) were co-evaporated on the hole transport layer to form an emitting layer. Next, bathocuproine (BCP) was evaporated on the emitting layer to form a hole blocking layer. Next, tris(8-hydroxyquinoline)aluminum(III) (Alq₃) was evaporated on the hole blocking layer to form an electron transport layer. Next, LiF was evaporated on the electron transport layer to form a buffer layer with a thickness of 10 Å. Finally, Al was evaporated on the buffer layer to form a cathode with a thickness of 1000 Å. Thus, completing fabrication of an organic light-emitting diode.

The synthetic processes of the disclosed green phosphorescent iridium complexes are simple, with a high yield and low cost.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A green phosphorescent iridium complex represented by Formula (I):

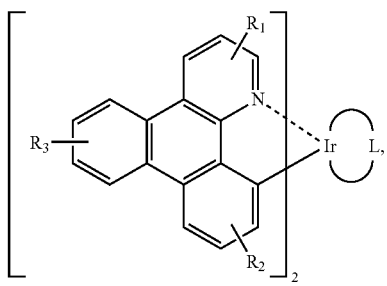

(I)

wherein

R1, R2 and R3 are, independently, hydrogen, halogen, substituted or non-substituted C1-6 alkyl, C1-6 alkoxy, cycloalkyl, substituted or non-substituted aryl, amino or heteroaryl; and L is an N—N ligand represented by one of the following formulae

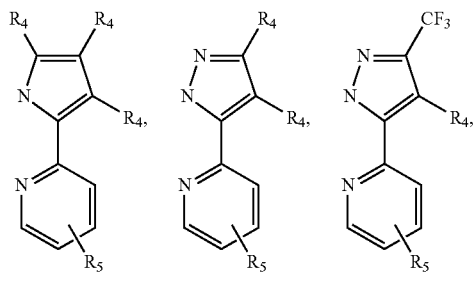

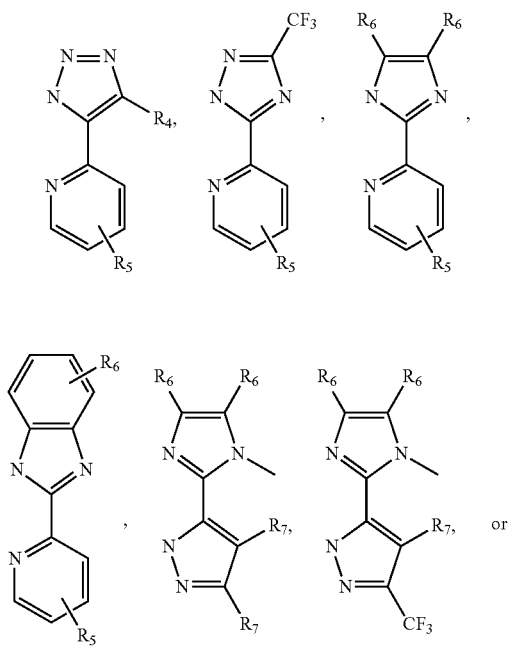

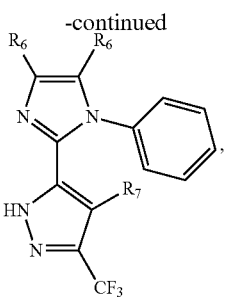

wherein R4-R7 are, independently, pyridine, quinoline, isoquinoline, pyrazine, pyrimidine, pyrrole, pyrazole, imidazole, indole, thiazole, isothiazole, oxazole, isoxazole, benzothiazole, benzoxazole, phenanthroline, methyl, ethyl, cyclohexyl, trifluoromethyl, benzyl, phenyl, naphthyl, diphenyl, anthryl, pyrenyl, phenanthryl, benzofuranyl or thiophenyl.

2. The green phosphorescent iridium complex as claimed in claim 1, wherein R1, R2 and R3 are pyridine, quinoline, isoquinoline, pyrazine, pyrimidine, pyrrole, pyrazole, imidazole, indole, thiazole, isothiazole, oxazole, isoxazole, benzothiazole, benzoxazole or phenanthroline.

3. The green phosphorescent iridium complex as claimed in claim 1, wherein R1, R2 and R3 are methyl, ethyl, cyclohexyl, trifluoromethyl, benzyl, phenyl, naphthyl, diphenyl, anthryl, pyrenyl, phenanthryl, benzofuranyl or thiophenyl.

4. An organic light-emitting diode, which comprises:

a cathode and an anode; and an emitting layer which comprises a green phosphorescent iridium complex as claimed in claim 1 disposed between the cathode and the anode.

5. The organic light-emitting diode as claimed in claim 4, wherein the organic light-emitting diode emits blue-green to yellow-green phosphorescence.

6. A green phosphorescent iridium complex represented by Formula (I):

(I)

wherein

R1, R2 and R3 are, independently, hydrogen, halogen, substituted or non-substituted C1-6 alkyl, C1-6 alkoxy, cycloalkyl, substituted or non-substituted aryl, amino or heteroaryl; and L is an N—N ligand represented by one of the following formulae

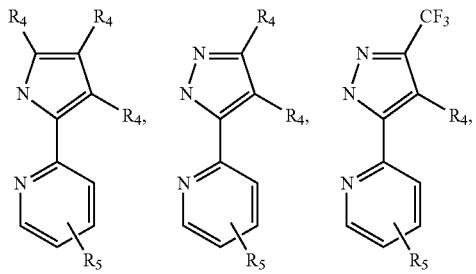

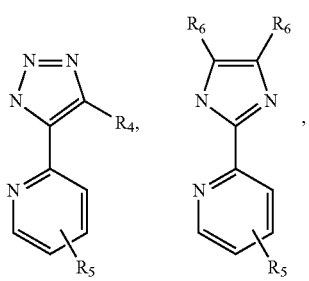

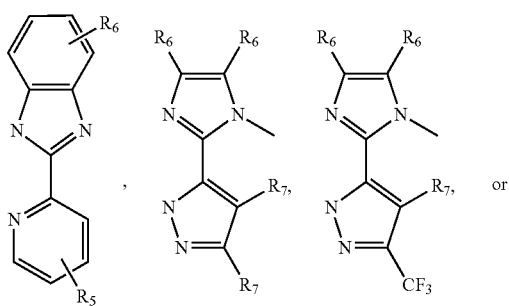

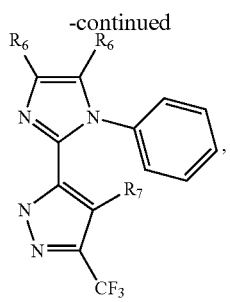

wherein R4-R7 are, independently, hydrogen, halogen, substituted or non-substituted C1-6 alkyl, C1-6 alkoxy, cycloalkyl, substituted or non-substituted aryl, amino or heteroaryl.

7. The green phosphorescent iridium complex as claimed in claim 6, wherein R1, R2 and R3 are pyridine, quinoline, isoquinoline, pyrazine, pyrimidine, pyrrole, pyrazole, imidazole, indole, thiazole, isothiazole, oxazole, isoxazole, benzothiazole, benzoxazole or phenanthroline.

8. The green phosphorescent iridium complex as claimed in claim 6, wherein R1, R2 and R3 are methyl, ethyl, cyclohexyl, trifluoromethyl, benzyl, phenyl, naphthyl, diphenyl, anthryl, pyrenyl, phenanthryl, benzofuranyl or thiophenyl.

9. The green phosphorescent iridium complex as claimed in claim 6, wherein R4-R7 are, independently, pyridine, quinoline, isoquinoline, pyrazine, pyrimidine, pyrrole, pyrazole, imidazole, indole, thiazole, isothiazole, oxazole, isoxazole, benzothiazole, benzoxazole or phenanthroline.

10. The green phosphorescent iridium complex as claimed in claim 6, wherein R4-R7 are, independently, methyl, ethyl, cyclohexyl, trifluoromethyl, benzyl, phenyl, naphthyl, diphenyl, anthryl, pyrenyl, phenanthryl, benzofuranyl or thiophenyl.

11. An organic light-emitting diode, which comprises:
a cathode and an anode; and
an emitting layer which comprises a green phosphorescent iridium complex as claimed in claim 6 disposed between the cathode and the anode.

12. The organic light-emitting diode as claimed in claim 11, wherein the organic light-emitting diode emits blue-green to yellow-green phosphorescence.

\* \* \* \* \*